(12) United States Patent
Sideris

(10) Patent No.: US 9,011,476 B2
(45) Date of Patent: Apr. 21, 2015

(54) METHOD AND APPARATUS FOR OCCLUDING A PHYSIOLOGICAL OPENING

(71) Applicant: Eleftherios B Sideris, Amarillo, TX (US)

(72) Inventor: Eleftherios B Sideris, Amarillo, TX (US)

( * ) Notice: Subject to any disclaimer, the term of this patent is extended or adjusted under 35 U.S.C. 154(b) by 10 days.

(21) Appl. No.: 13/922,132

(22) Filed: Jun. 19, 2013

(65) Prior Publication Data

US 2013/0338696 A1    Dec. 19, 2013

Related U.S. Application Data

(62) Division of application No. 12/803,851, filed on Jul. 8, 2010, now abandoned.

(60) Provisional application No. 61/270,455, filed on Jul. 9, 2009.

(51) Int. Cl.
*A61M 29/00* (2006.01)
*A61B 17/12* (2006.01)

(52) U.S. Cl.
CPC ............................... *A61B 17/12022* (2013.01)

(58) Field of Classification Search
USPC ............. 128/898; 604/103.01, 500, 509, 510, 604/543; 606/151, 192, 194, 195, 198, 213, 606/215; 623/1.11
See application file for complete search history.

(56) References Cited

U.S. PATENT DOCUMENTS 5,176,692 A * 1/1993 Wilk et al. ..................... 606/151

* cited by examiner

*Primary Examiner* — Vy Q Bui
(74) *Attorney, Agent, or Firm* — Buche & Associates, P.C.; John K. Buche

(57) ABSTRACT

A method and apparatus for suture-less placement of an occluding patch in which release of the device can be accelerated. In one embodiment, an inactive form of an adhesive is applied on the area of the patch that will come into contact with cardiac tissue; this allows for the introduction and necessary manipulation of the catheter system until activation of the adhesive occurs. In accordance with one aspect of the invention, the adhesive properties of certain polymeric materials are relied upon rather than their ability to cure or harden into a specific shape. In another embodiment, the patch is immediately released utilizing a detaching mechanism on the balloon or the balloon catheter which supports the patch; the patch along with the inflated balloon remain on the cardiac structure occluding the opening.

7 Claims, 7 Drawing Sheets

METHOD AND APPARATUS FOR OCCLUDING A PHYSIOLOGICAL OPENING

CROSS-REFERENCE TO RELATED APPLICATIONS

The present application is a divisional application of application Ser. No. 12/803,851, filed on Jul. 8, 2010. Application Ser. No. 12/803,851 is entitled to the benefit of the filing date of the prior-filed provisional application No. 61/270,455, filed on Jul. 9, 2009.

STATEMENT REGARDING FEDERALLY SPONSORED RESEARCH OR DEVELOPMENT

Not applicable.

BACKGROUND OF THE INVENTION

1. Field of Invention

This invention relates generally to cardiovascular devices, intended to occlude circulatory communications that may be or may become detrimental to patient health. More specifically, this invention encompasses accelerated release methods for an occlusion methodology involving sutureless delivery of an occlusion patch to a physiological opening.

2. Background

Compromised health may be caused by cardiovascular structures that adversely affect the proper flow of blood. Such structures may be abnormalities that affect a relatively small subset of the population, and others may be common and not normally pathogenic, yet become so due to extrinsic causes. Examples of the former are congenital heart defects including Atrial Septal Defect (ASD), Ventricular Septal Defect (VSD), and Patent Ductus Arteriosus (PDA), and examples of the latter are normal cardiac structures such as Patent Foramen Ovale (PFO) and Left Atrial Appendage (LAA). The above mentioned structures are generally characterized by a hole or opening, which allows for fluid communication between cardiac chambers and/or blood vessels.

Congenital heart defects can cause an abnormal distribution of cardiovascular pressures and the dilution of oxygenated blood, which can significantly reduce cardiac pumping efficiency. Normal cardiac structures can sometimes become pathogenic by functioning as a location of blood clot formation, as in the LAA, or as a path by which blood clots can travel to the brain, as in PFO. Additionally, modifications to cardiovascular structures, which can cause anomalous blood flow, may be intentionally created by a physician in order to accommodate a certain procedure or to elicit some therapeutic effect. An example of this is the creation of a hole in the cardiac wall, in order to insert catheters and have direct access to cardiac structures such as valves. One treatment option for such cardiovascular structures is to occlude the communication using a surgically or percutaneously implanted device. Patents have been issued for several such devices including U.S. Pat. No. 3,874,388 to King et al., U.S. Pat. No. 4,917,089 to Sideris, and U.S. Pat. No. 5,725,552 to Kotula et al. Although these patents vary in many ways, their common attribute is that they include the concept of a metallic frame, intended to provide permanent support that maintains the device on the cardiac structure. Although metallic occlusive devices are widely used, they carry certain risks including wire fractures, perforations, and potential leaching of toxic materials.

Devices containing no metallic materials can potentially eliminate some of these risks. Non-metallic occlusive devices have been proposed in the prior art, including: U.S. Pat. No. 5,192,301 to Kamiya et al., which appears to describe a deformable plug made from a shape memory polymer; U.S. Pat. No. 5.634,936 to Linden et al. which appears to describe a device that includes a "self-hardening" polymeric material; U.S. Pat. No. 6,238,416 to Sideris, which appears to describe a balloon deliverable polymeric device; and U.S. patent application Ser. No. 11/728,906 to Opolski et al. describing a device using a polymeric wire frame. To the inventors' knowledge, only one of these patents covers a device that is in commercial use; this is U.S. Pat. No. 6,238,416 to Sideris, which patent is hereby incorporated by reference herein in its entirety.

The Sideris '416 patent describes a method of suture-less patch placement to correct a physiological opening in the form of a heart defect comprising a hole. The patch is first attached to a deflated balloon which is placed distally to the hole using special delivery catheters. The balloon is inflated with fluid and the patch is positioned upon the hole. After a specified coagulation/endothelialization period of time, the balloon is deflated and removed through a small hole in the patch, leaving the patch to occlude the defect. Practically, the coagulation/endothelialization process serves to attach/adhere the patch onto the cardiac tissue. This process requires an extended period of time, which can be dependent on the patch material. The extended period of time required for completion of this process makes the procedure inconvenient compared with other occlusive techniques and devices.

SUMMARY OF THE INVENTION

In view of the foregoing and other considerations, the present invention relates to a method and apparatus for suture-less placement of an occluding patch in which release of the device can be accelerated. The importance and potential of the invention is significant, since the defects are corrected conveniently on an outpatient basis and potential complications such as thrombosis or infection are diminished.

Attachment of the patch and/or device release can be accelerated by two methods. In one embodiment, an inactive form of an adhesive is applied on the area of the patch that will come into contact with cardiac tissue; this allows for the introduction and necessary manipulation of the catheter system until activation of the adhesive occurs. In another embodiment, the patch is immediately released utilizing a detaching mechanism on the balloon or the balloon catheter which supports the patch; the patch along with the inflated balloon remain on the cardiac structure occluding the opening. The patch and balloon are immobilized, either by the shape (double disk, spherical, etc.) and fit of the balloon in the opening, or by a thread or an anchoring tube which is connected to the occluder and can be manipulated from the percutaneous entry point (usually the groin). All materials used for this device may be bio-degradable and are progressively metabolized or eroded, and in the case of the patch, replaced by natural tissue.

In accordance with one aspect of the invention, the adhesive properties of certain polymeric materials are relied upon rather than their ability to cure or harden into a specific shape. Indeed, the use of polymeric self-hardening materials has been described in U.S. Pat. No. 5,634,936; these materials can be delivered by a catheter to the area of the defect and hardened in situ by change the pH or ionic concentration, exposure to light or thermal energy.

Those of ordinary skill in the art having the benefit of the present disclosure will appreciate that accelerated patch attachment using an adhesive or immediate patch release using temporary support of a bio-absorbable thread can find several other applications, including but not limited to heart valves, internal vascular work and even coronary artery surgery. Furthermore, surgeons could use the suture-less technique to avoid suture related injury during surgery.

BRIEF DESCRIPTION OF THE DRAWINGS

The present invention is best understood with reference to the following detailed description of embodiments of the invention when read in conjunction with the attached drawings, in which like numerals refer to like elements, and in which.

DETAILED DESCRIPTION OF PREFERRED EMBODIMENTS OF THE INVENTION

Figure 1:
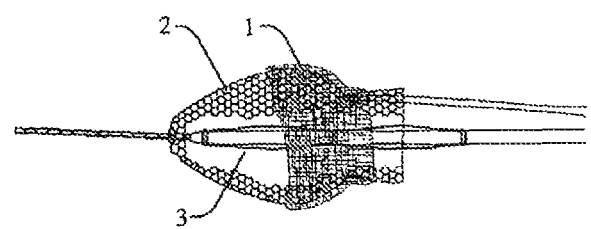
FIG. 1 is a side view of in introduction assembly for delivery and placement of an occlusion device (patch) into a physiological opening, with adhesive placed on a proximal portion of the patch prior to implantation.
Figure 2:
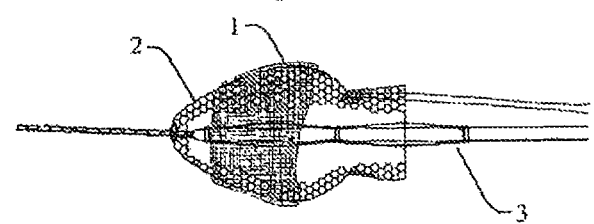
FIG. 2 is a side view of in introduction assembly for delivery and placement of an occlusion device (patch) into a physiological opening, with adhesive placed on a distal portion of the patch prior to implantation.
Figure 3:
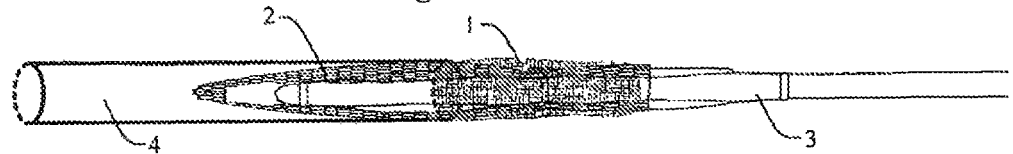
FIG. 3 is a side view of the introduction assembly of FIG. 1 with a balloon mounted patch inserted into a short by-pass sheath; the proximal end of the patch extends outside of the short by-pass sheath and is coated by the inactive adhesive.
Figure 4:
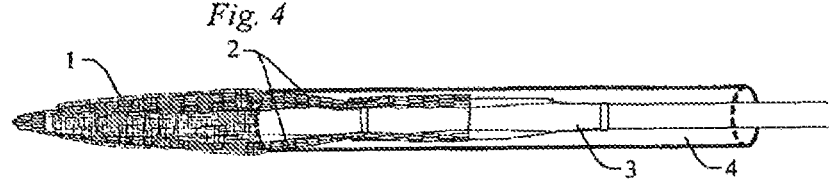
FIG. 4 is a side view of the introduction assembly of FIG. 2 with a balloon mounted patch inserted into a short by-pass sheath; the distal end of the patch extends outside of the short by-pass sheath and is coated by the inactive adhesive.
Figure 5:
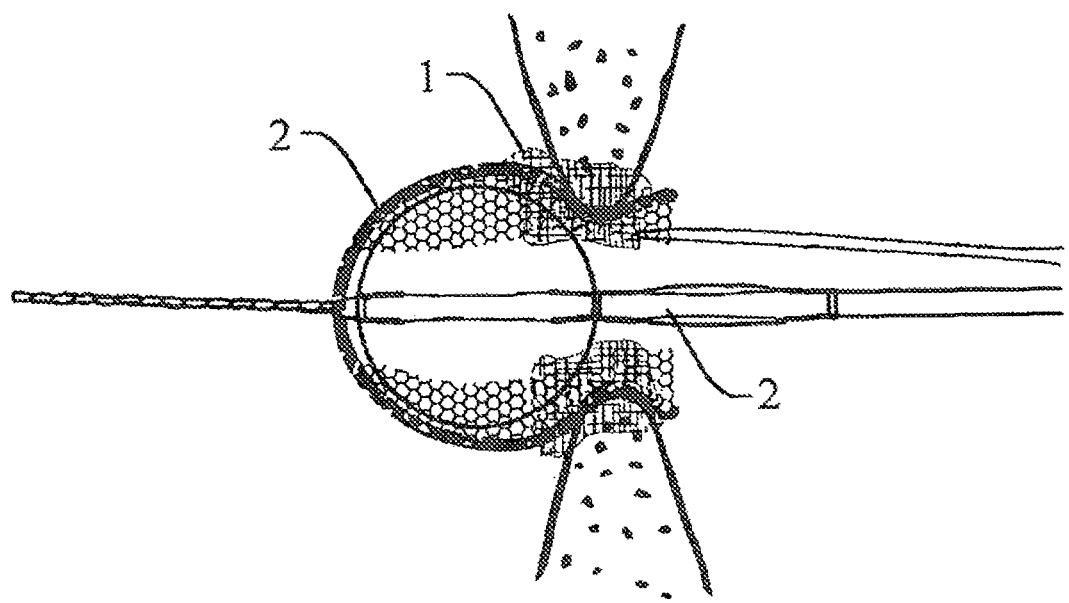
FIG. 5 is a side cross-sectional view of a correctly positioned and inflated patch, where the adhesive is coming into contact with the cardiovascular opening.

In the disclosure that follows, in the interest of clarity, not all features of actual implementations are described. It will of course be appreciated that in the development of any such actual implementation, as in any such project, numerous engineering and technical decisions must be made to achieve the developers specific goals and subgoals (e.g., compliance with system and technical constraints), which will vary from one implementation to another. Moreover, attention will necessarily be paid to proper medical and engineering practices for the environment in question. It will be appreciated that such development efforts might be complex and time-consuming, outside the knowledge base of typical laymen, but would nevertheless be a routine undertaking for those of ordinary skill in the relevant fields.

The present invention encompasses methods for accelerated attachment and/or release of an occlusive device placed at the site of a physiological opening, especially but not solely for applications in the cardiovascular field. The implantation procedure of one such occlusive device is described in detail in our previous U.S. Pat. No. 6,238,416 (previously incorporated by reference herein) and as such will only be described herein to the extent that it is necessary to illustrate the accelerated attachment/release aspects of the present invention.

Method I

In accordance with one embodiment of the invention, accelerated attachment of an occlusive patch can be achieved by the application of an inactive form of an adhesive onto the patch prior to implantation. The adhesive can be polyethylene glycol based with end/side groups that can react with each other and the surrounding tissue to form strong chemical bonds. One adhesive believed to be suitable for the purposes of the invention is the commercially available product COSEAL™ surgical sealant, distributed by Baxter, Deerfield, Ill. More generally, the adhesive can take the form of a liquid, gel, or solid and may be chemically or mechanically bound to the patch. Said adhesive may be applied onto the patch, either as part of the manufacturing process, directly before implantation, or during implantation.

In one embodiment, the adhesive is placed on the entire patch or on a selected portion of the patch, whichever is best suited for maximal apposition to the specific cardiovascular opening. Once the device is positioned correctly in the appropriate physiological opening, the adhesive may be activated directly by several methods including pH changes of the surrounding blood/tissue, temperature changes induced by the normal body temperature or from input of thermal energy, and input of electromagnetic energy including, but not limited to the UV, visible, and IR spectrums.

In an alternative embodiment of the invention, the adhesive may be activated indirectly by a biocompatible initiator that is itself activated by the above mentioned methods. It is contemplated that such an initiator may be injected into the blood stream around the defect before or during device implantation, in a way that adequately coats the surface of the defect and/or the device. The initiator may also be applied directly onto the patch prior to implantation.

In one embodiment, a two stage adhesive is used with a transition that is sensitive to pH. Referring to FIG. 1, the adhesive 1, in its first stage, is applied to all or to a portion of the patch 2. The patch 2, which is mounted on a balloon catheter 3, is placed into a short by-pass sheath 4. Any excessive adhesive material is wiped out by introduction into the by-pass sheath. In one embodiment, the balloon-mounted patch can be placed in the short by-pass sheath prior to application of the adhesive. A portion of the patch can be made to extend outside of the by-pass sheath and can then be coated with the inactive adhesive. It is then pushed or pulled completely into the by-pass sheath, wiping away any excessive adhesive material. Subsequently the balloon mounted patch is introduced through the hemostat valve of a long sheath, which is already implanted in the patient, and is advanced to the appropriate physiological opening. Activation occurs automatically due to the slight alkalinity of blood, but the reaction rate is slow enough to allow for device manipulation, balloon inflation, and placement.

Figure 6:
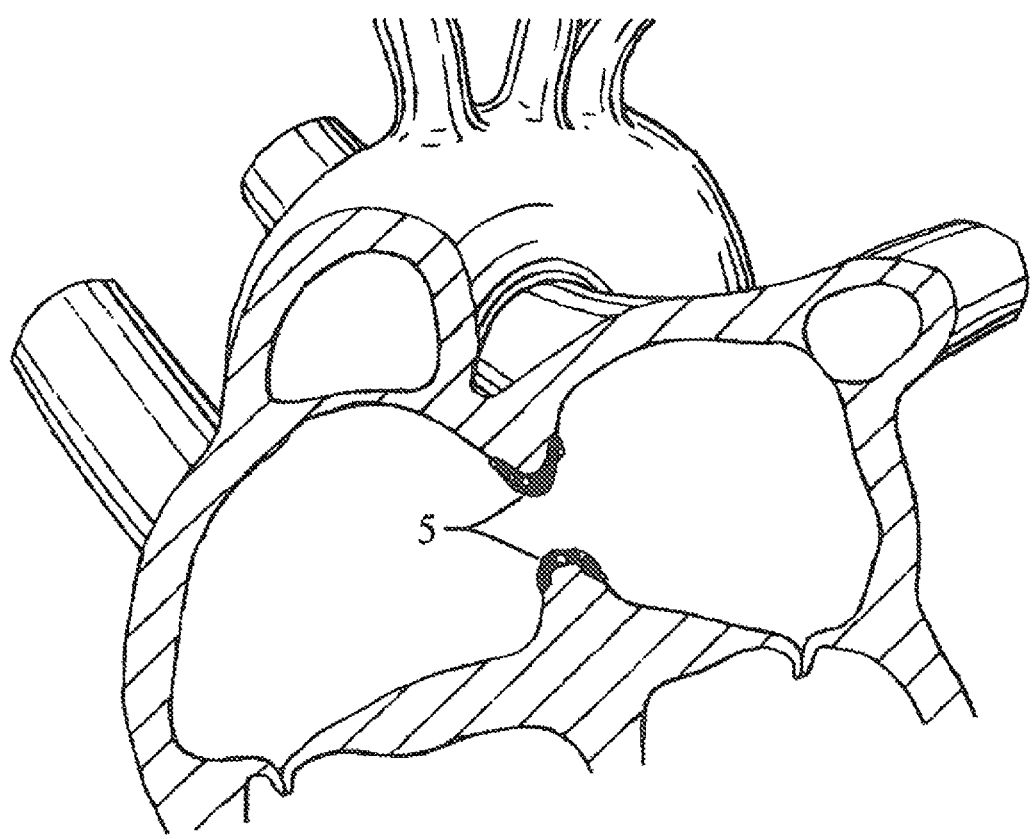
FIG. 6 is a side cross-sectional view of an ASD that has been coated by an initiator.
Figure 7:
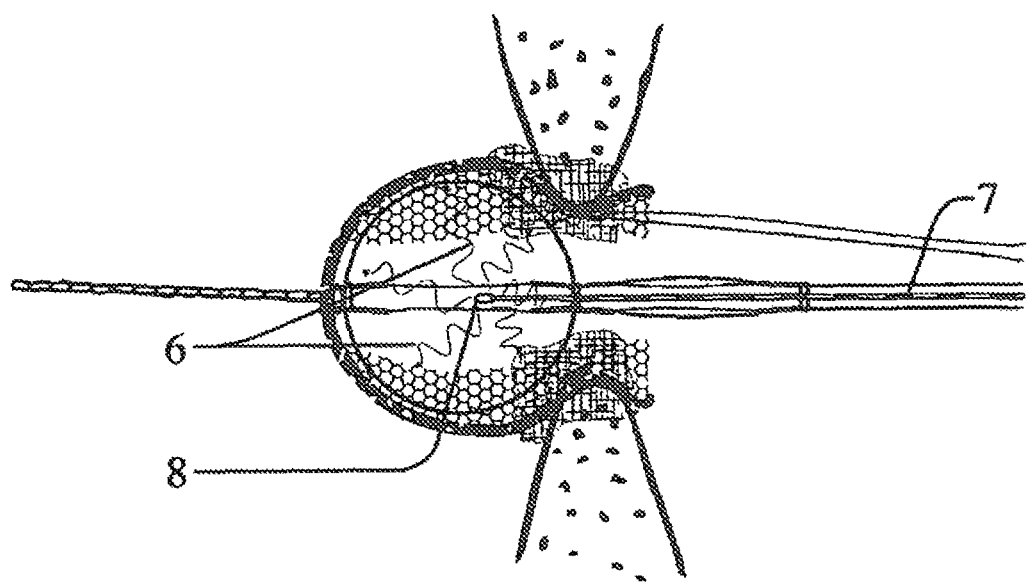
FIG. 7 is a side cross-sectional view of a correctly positioned and inflated patch being irradiated from inside the balloon.

In another embodiment, referring to FIG. 6, an initiator 5 that is activated by electromagnetic radiation of a certain frequency is injected near the physiological opening intended for occlusion. The process effectively coats the opening with the initiator. The inactive adhesive is then applied to all or to a portion of the patch and the device is placed into a short by-pass sheath. Any excessive adhesive material is wiped out by introduction into the by-pass sheath. An adhesive can be applied as described with reference to the previous embodiment. Subsequently the balloon mounted patch is introduced through the hemostat valve of a long sheath, which is already implanted in the patient, and is advanced to the appropriate physiological opening, The balloon is inflated and the device is positioned appropriately to occlude the physiological opening. Electromagnetic radiation 6 is delivered to the initiator through an optical fiber 7 that ends in a diffusing tip 8. The optical fiber may be advanced to the physiological opening through the balloon catheter to the balloon and irradiation may be carried out from inside the balloon assuming that the balloon and inflating solution do not absorb the radiation. Alternatively, the optical fiber may be advanced to the physiological opening independently and irradiation may be carried out from outside the balloon. The electromagnetic radiation may be, for example, in the ultraviolet (UV), visible, or infrared spectrums.

In yet another embodiment, an initiator that is activated by electromagnetic radiation of a certain frequency is mixed with the inactive adhesive la. The mixture is then applied to all or to a portion of the patch and the device is placed into a short by-pass sheath. Any excessive mixture material is wiped out by introduction into the by-pass sheath. An adhesive can be applied as described above. Subsequently the balloon mounted patch is introduced through the hemostat valve of a long sheath, which is already implanted in the patient, and is advanced to the appropriate physiological opening. The balloon is inflated and the device is positioned appropriately to occlude the physiological opening. Electromagnetic radiation can then be delivered to the initiator by the methods presented in the previous embodiment.

Method II

In accordance with an alternative embodiment of the invention, accelerated release of the occlusive device without accelerated attachment of the patch can be achieved by incorporating a detachment mechanism into the balloon catheter. Such a mechanism allows for separation of the inflated balloon from the catheter shaft after correct positioning and inflation of the device. Both the balloon and the surrounding patch then remain, occluding the defect, while the remaining materials are extracted. The balloon provides adequate support for a long enough period of time in order for the patch to become attached to the cardiac tissue through the normal coagulation/endothelialization process. Once the supporting function of the balloon is no longer necessary, it is deflated actively or passively in order for the device volume to be reduced to the size that is necessary for effective occlusion. The balloon may be made from synthetic or natural materials that are either bio-degradable or bio-stable, as would be apparent to those of ordinary skill in the art. Additionally, the balloon may be compliant or non-compliant and may be formed into a regular shape (sphere, disk, etc.) or an organic shape in order to more appropriately occlude a given physiological opening. The balloon may also have multiple segments of similar or different shapes that can be independently inflated to accommodate different physiological openings.

Depending on the physiological opening intended for closure and the ability of the balloon to remain immobilized adequately by its shape, an additional support mechanism may be incorporated, This mechanism may be a thread, shaft, or tube that remains attached to the balloon and/or patch and extends to or beyond the percutaneous opening by which access was gained to the subcutaneous tissue/space or to the circulatory system. The extension may then be actively attached to the surrounding tissue. Said attachment may be accomplished through suturing and/or through the use of a secondary piece of material (anchor) that can be embedded into the surrounding tissue. This attachment should hold the extension in tension or compression in order to adequately immobilize the balloon onto the physiological opening.

Figure 8:
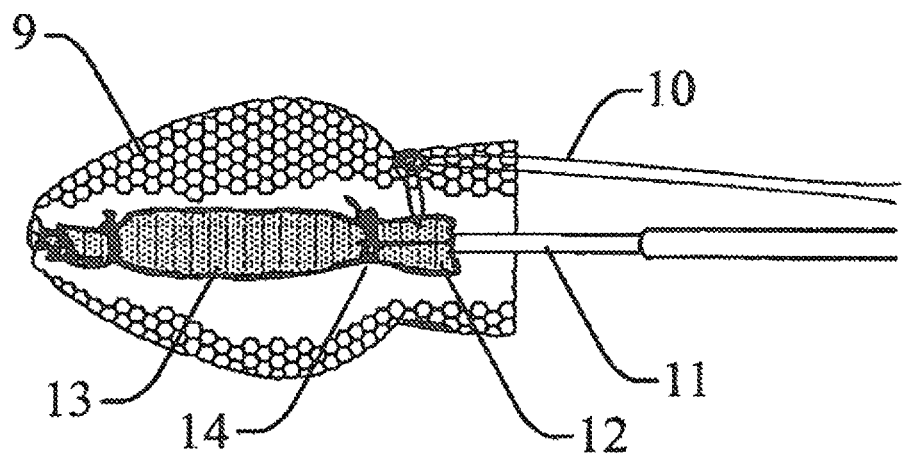
FIG. 8 is a side view of an introduction assembly in accordance with one embodiment of the invention prior to implantation.
Figure 9:
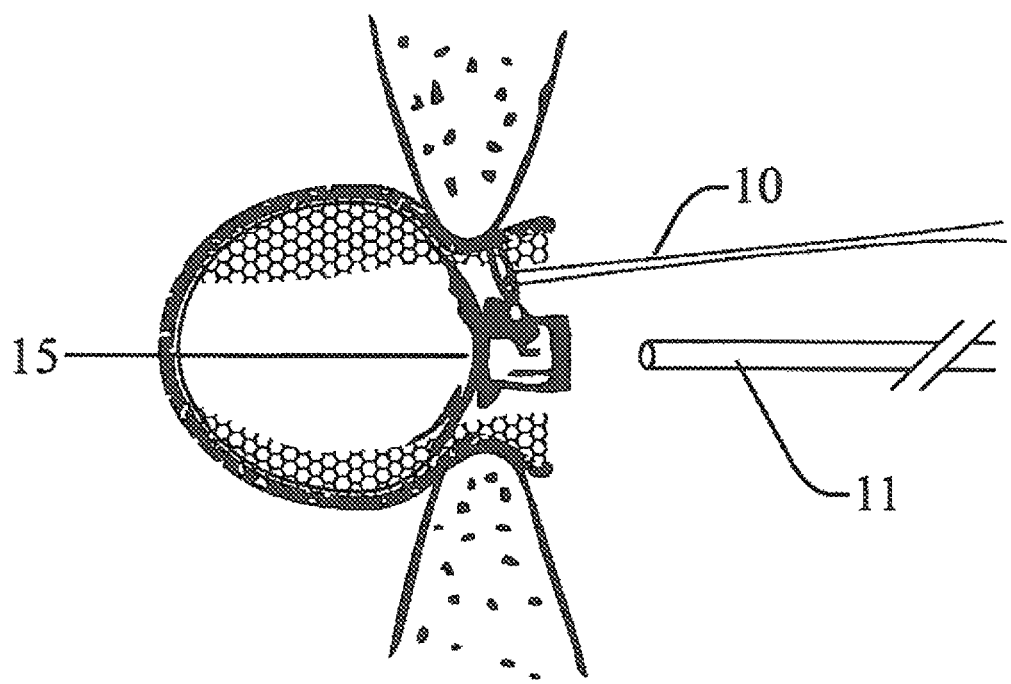
FIG. 9 is a side cross-sectional view of an introduction assembly positioned and inflated after the balloon catheter has been separated into its two components.
Figure 10:
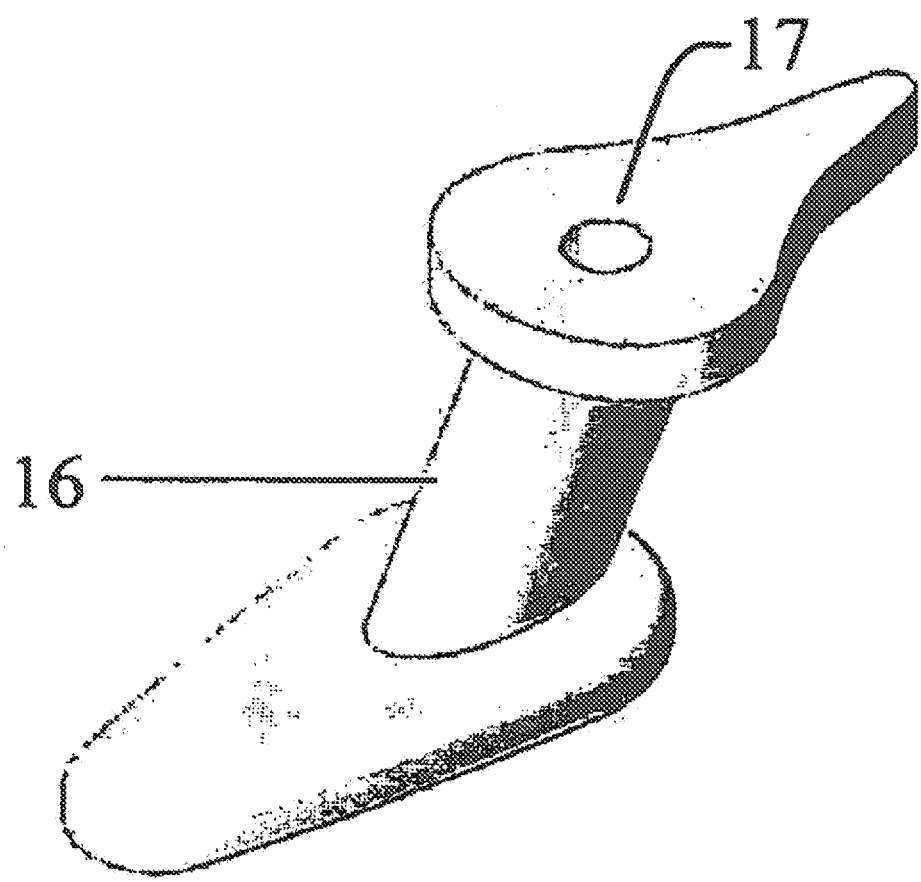
FIG. 10 is a perspective view of an apparatus used in one embodiment of the invention to circumvent the suturing procedure.

Referring now to FIGS. 8 through 10, in one embodiment, the device is comprised of a balloon catheter and the mounted patch 9. A biodegradable thread 10 is attached to the balloon/patch and extends in the direction of the balloon catheter. The catheter portion 11 of the balloon catheter is independent and fits into a hole, in the form of a neck 12, on one end of the balloon 13. The balloon is held in place over the catheter by an elastic material in tension 14, which covers a portion of the neck. Depending on the thickness of the catheter, a metal stylet may be inserted into the catheter to provide support during implantation. For implantation, the balloon mounted patch is first placed into a short by-pass sheath. It is then introduced through the hemostat valve of a long sheath, which is already implanted in the patient's vasculature, and is advanced to the appropriate physiological opening. If a metal stylet was used, it is removed, and the balloon is inflated and positioned at the site of the physiological opening. Once correct placement has been verified, the catheter is pulled out of the balloon, and the remaining tension of the elastic piece automatically seals the neck (synching) 15, preventing balloon deflation. The introducing sheath is then pulled over the extending biodegradable thread and is removed from the vasculature. The biodegradable thread, which extends outside of the percutaneous entry point, is pulled to ensure immobilization of the balloon/patch and it is sutured beneath the skin.

A simple improvement of this embodiment can be made by using an anchor comprising a small piece of relatively rigid material 16 with a central shaft 17, through which the thread can be passed, intended to facilitate or circumvent the suturing process. This piece can be made from biodegradable materials. Such an anchor would hold the thread in tension, either by wrapping the thread around it and/or by forming a knot and/or by a clamping mechanism. The material would then be safely embedded under the skin.

In yet another embodiment, the same setup as the previous embodiment is used with the exception of a screw mechanism instead of a synching mechanism connecting the two pieces of the balloon catheter. In addition to the screw mechanism, a one-way valve is incorporated in the balloon to prevent balloon deflation after the catheter has been detached. All materials comprising the screw mechanism and one-way valve are preferably biodegradable.

In another embodiment, the device is comprised of a balloon catheter and the mounted patch. The catheter is made from a biodegradable material and it is permanently attached to the catheter, Depending on the thickness of the catheter, a metal stylet may be inserted into the catheter to provide support during implantation. For implantation, the balloon mounted patch is first placed into a short by-pass sheath, It is then introduced through the hemostat valve of a long sheath, which is already implanted in the patient, and is advanced to the appropriate physiological opening. If a metal stylet was used, it is removed, and the balloon is inflated and a positioned on or about the physiological opening. Once correct placement has been verified, the introducing sheath is pulled over the balloon catheter and is removed from the patient. The portion of the catheter that extends outside of the percutaneous opening can then be capped to prevent balloon deflation, and a optionally a secondary piece can be advanced over the catheter and embedded under the skin to act as an anchor. Such an anchor piece would be attached to the catheter by a ratchet, screw, or clamping mechanism and it should hold the balloon catheter in tension or compression to maintain the balloon/patch immobile on the physiological opening.

At least one embodiment of the invention has been described herein solely for the purposes of illustrating the invention in its various aspects. It is contemplated and to be explicitly understood that various substitutions, alterations, and/or modifications, including but not limited to any such implementation variants and options as may have been specifically noted or suggested herein, including inclusion of technological enhancements to any particular method step or system component discovered or developed subsequent to the date of this disclosure, may be made to the disclosed embodiments of the invention without necessarily departing from the technical and legal scope of the invention as defined in the following claims.

The invention claimed is:

1. A method of placing a patch at the site of a physiological opening comprising:
   (a) providing a patch of a polymeric material placed on an uninflated distal balloon to create a balloon-patch assembly;
   (b) providing a catheter, detachably coupled to said balloon;
   (c) utilizing said catheter to place said patch and said balloon proximate to the physiological opening;
   (d) inflating said balloon to bring said balloon-patch assembly in contact with said physiological opening;
   (e) detaching said catheter from said inflated balloon-patch assembly and withdrawing said catheter; and
   (f) providing an elongate support mechanism for immobilizing said balloon-patch assembly; wherein said elongate support mechanism comprises a thread extending from said balloon-patch assembly to a percutaneous opening.

2. A method in accordance with claim 1, further comprising:
   (g) allowing said balloon to deflate automatically following a coagulation/endothelialization period.

3. A method in accordance with claim 1, further comprising:
   (g) attaching a proximal end of said support mechanism to tissue surrounding the percutaneous opening.

4. A method in accordance with claim 3, further comprising an anchor for attachment of said proximal end of said support mechanism to said percutaneous opening.

5. A method in accordance with claim 1 wherein an adhesive in inactive form is applied to said patch.

6. A method in accordance with claim 5 wherein said adhesive is:
   a two-stage adhesive with a transition that is sensitive to pH;
   activated by injecting an adhesive initiator around the physiological opening;
   activated by exposing the adhesive to electromagnetic energy wherein said electromagnetic energy comprises radiation in any of the group consisting essentially of either:
   ultraviolet spectrum,
   visible spectrum, and
   infrared spectrum; or,
   activated by exposing the adhesive to ambient or applied thermal energy.

7. A method of placing a patch at the site of a physiological opening comprising:
   (a) applying an adhesive in an inactive form to a patch of a polymeric material wherein said adhesive is:
   a two-stage adhesive with a transition that is sensitive to pH;
   activated by injecting an adhesive initiator around the physiological opening;
   activated by exposing the adhesive to electromagnetic energy wherein said electromagnetic energy comprises radiation in any of the group consisting essentially of either:
   ultraviolet spectrum,
   visible spectrum, and
   infrared spectrum; or,
   activated by exposing the adhesive to ambient applied thermal energy;
   (b) placing the patch of polymeric material on an uninflated distal balloon to create a balloon-patch assembly;
   (c) providing a catheter, detachably coupled to said balloon;
   (d) utilizing said catheter to place said patch and said balloon proximate to the physiological opening;
   (e) inflating said balloon to bring said balloon-patch assembly in contact with said physiological opening;
   (f) detaching said catheter from said inflated balloon-patch assembly and withdrawing said catheter;
   (g) providing an elongate support mechanism for immobilizing said balloon-patch assembly wherein said support mechanism comprises a thread extending from said balloon-patch assembly to a percutaneous opening; and,
   (h) utilizing an anchor to attach a proximal end of said support mechanism to tissue surrounding the percutaneous opening.

* * * * *